United States Patent
Nagata et al.

(10) Patent No.: US 11,083,227 B2
(45) Date of Patent: Aug. 10, 2021

(54) FLAVOR INHALER

(71) Applicant: JAPAN TOBACCO INC., Tokyo (JP)

(72) Inventors: Hisanori Nagata, Tokyo (JP); Yukio Sone, Tokyo (JP); Naoto Yamashita, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 282 days.

(21) Appl. No.: 16/266,794

(22) Filed: Feb. 4, 2019

(65) Prior Publication Data

US 2019/0166915 A1 Jun. 6, 2019

Related U.S. Application Data

(63) Continuation of application No. PCT/JP2016/072982, filed on Aug. 4, 2016.

(51) Int. Cl.
*A24F 40/60* (2020.01)
*A24F 40/40* (2020.01)
(Continued)

(52) U.S. Cl.
CPC ............. *A24F 40/60* (2020.01); *A24F 40/40* (2020.01); *A24F 40/51* (2020.01); *A24F 40/65* (2020.01); *A61M 15/06* (2013.01); *A24F 40/10* (2020.01)

(58) Field of Classification Search
CPC .......... A24F 40/60; A24F 40/65; A24F 40/51; A24F 40/10; A24F 40/40
(Continued)

(56) References Cited

U.S. PATENT DOCUMENTS 5,469,505 A * 11/1995 Gattey ................ H04M 1/05
379/430
6,223,744 B1 * 5/2001 Garon .................. A61M 15/00
128/200.14
(Continued)

FOREIGN PATENT DOCUMENTS

CN 2047485 U 11/1989
CN 203001618 U 6/2013
(Continued)

OTHER PUBLICATIONS

Chinese Office Action and Search Report for Chinese Application No. 201680089198.2, dated Dec. 2, 2020, with English translation.
(Continued)

*Primary Examiner* — Alexander Gilman
(74) *Attorney, Agent, or Firm* — Birch, Stewart, Kolasch & Birch, LLP

(57) ABSTRACT

The present invention provides a flavor inhaler includes a flavor releasing unit provided with at least one holding part for storing a flavor component and an aerosol-forming substrate, an aerosol generation part for generating an aerosol containing the flavor component from the contents of the holding part, and a flavor providing part configured to direct the aerosol generated by the aerosol generation part to a user, a speaker unit provided with an oscillator for generating a sound wave and a speaker interface for transmitting the sound wave from the oscillator to the user's skull, and a controller for controlling the flavor releasing unit and the speaker unit so that generation of the aerosol and generation of the sound wave are in coordination with each other.

7 Claims, 5 Drawing Sheets

(51) Int. Cl.
  *A24F 40/51* (2020.01)
  *A24F 40/65* (2020.01)
  *A61M 15/06* (2006.01)
  *A24F 40/10* (2020.01)
(58) Field of Classification Search
  USPC .............................................................. 131/329
  See application file for complete search history.

(56) References Cited

U.S. PATENT DOCUMENTS

| | | | | |
|---|---|---|---|---|
| 6,971,383 | B2* | 12/2005 | Hickey | A61M 15/0085 |
| | | | | 128/203.12 |
| 7,508,932 | B1* | 3/2009 | Bergh | H04B 1/385 |
| | | | | 379/430 |
| D808,007 | S* | 1/2018 | Denega | D24/110 |
| 9,877,517 | B2* | 1/2018 | Liu | A24F 1/30 |
| 9,888,714 | B2* | 2/2018 | Cameron | A24F 47/008 |
| 9,936,736 | B2* | 4/2018 | Cameron | H02J 7/00 |
| 9,956,360 | B2* | 5/2018 | Germinario | A61M 15/025 |
| 10,004,269 | B2* | 6/2018 | Xiang | H02J 7/007 |
| 10,039,327 | B2* | 8/2018 | Cameron | A24F 47/008 |
| 10,058,128 | B2* | 8/2018 | Cameron | H05B 3/12 |
| 10,391,270 | B2* | 8/2019 | Adams | A61M 15/00 |
| 10,561,172 | B2* | 2/2020 | Armoush | A24F 47/008 |
| 10,617,150 | B2* | 4/2020 | Cameron | A61M 15/06 |
| 10,806,876 | B2* | 10/2020 | O'Sullivan | A61M 16/0866 |
| 2005/0284901 | A1* | 12/2005 | Taylor | H04R 1/105 |
| | | | | 224/181 |
| 2014/0096782 | A1* | 4/2014 | Ampolini | A24F 47/008 |
| | | | | 131/328 |
| 2014/0278258 | A1 | 9/2014 | Shafer | |
| 2015/0122276 | A1 | 5/2015 | Johnson et al. | |
| 2015/0128971 | A1 | 5/2015 | Verleur et al. | |
| 2015/0181930 | A1* | 7/2015 | Liu | A24F 47/008 |
| | | | | 131/329 |
| 2017/0100551 | A1* | 4/2017 | Baldwin | A61M 15/0025 |
| 2017/0169184 | A1* | 6/2017 | Doswell | A61B 5/1112 |
| 2017/0238596 | A1 | 8/2017 | Matsumoto et al. | |

FOREIGN PATENT DOCUMENTS

| | | |
|---|---|---|
| CN | 204275027 U | 4/2015 |
| CN | 204275207 U | 4/2015 |
| CN | 104621716 A | 5/2015 |
| CN | 204409582 U | 6/2015 |
| CN | 204411431 U | 6/2015 |
| CN | 104812260 A | 7/2015 |
| CN | 205108619 U | 3/2016 |
| JP | 2002-209570 A | 7/2002 |
| JP | 2015-502172 A | 1/2015 |
| JP | 2015-107056 A | 6/2015 |
| TW | 201347691 A | 12/2013 |
| TW | 201507637 A | 3/2015 |
| TW | 201528977 A | 8/2015 |
| WO | WO 2013/025921 A1 | 2/2013 |
| WO | WO 2013/137084 A1 | 9/2013 |
| WO | WO 2014/058678 A1 | 4/2014 |
| WO | WO 2016/075746 A1 | 5/2016 |

OTHER PUBLICATIONS

Korean Office Action for Korean Application No. 10-2019-7003114 dated Aug. 19, 2020 with English Translation.
Canadian Office Action, dated Apr. 9, 2020, for Canadian Application No. 3,032,761.
Extended European Search Report, dated Mar. 19, 2020, for European Application No. 16911639.9.
Office Action dated Mar. 28, 2017 for TaiwanesePatent Application No. 105124956.
International Search Report for PCT/JP2016/072982 (PCT/ISA/210) dated Oct. 4, 2016.

* cited by examiner

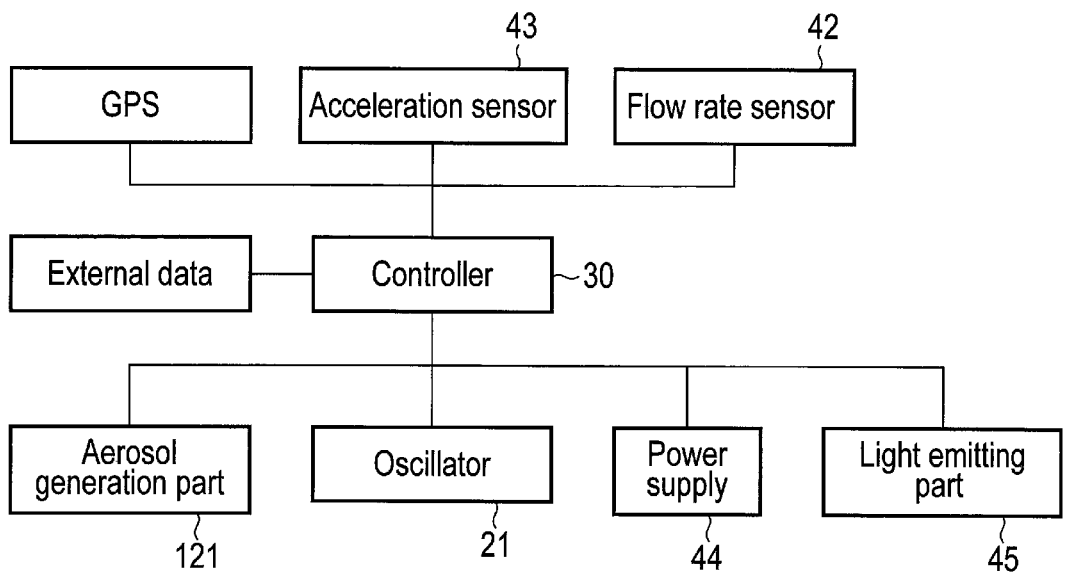
F I G. 5
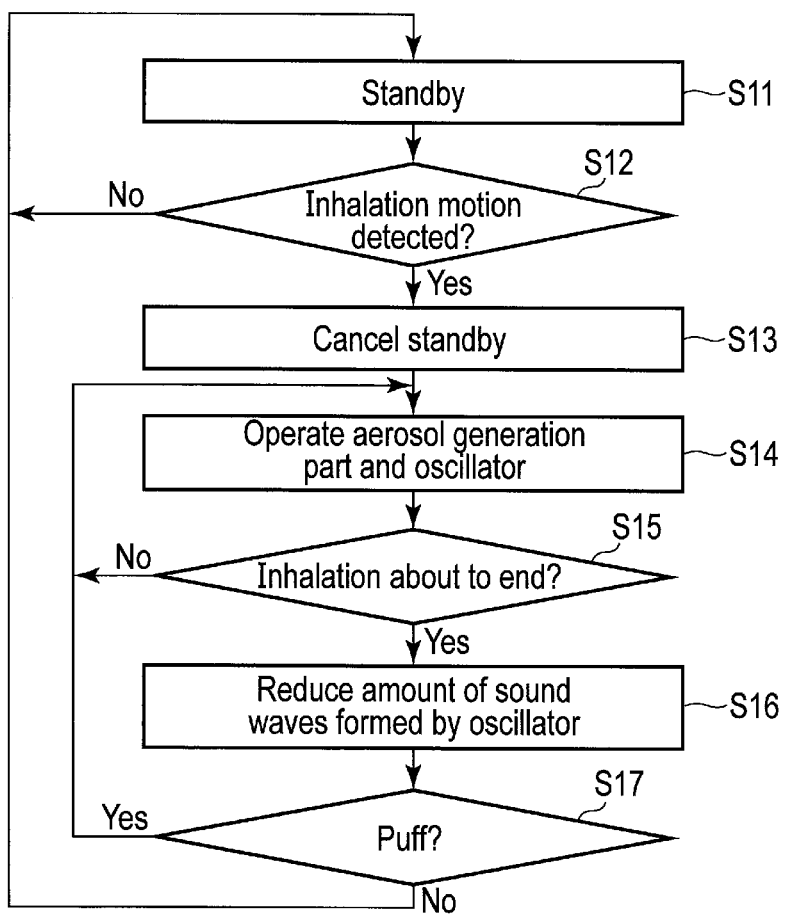
F I G. 6

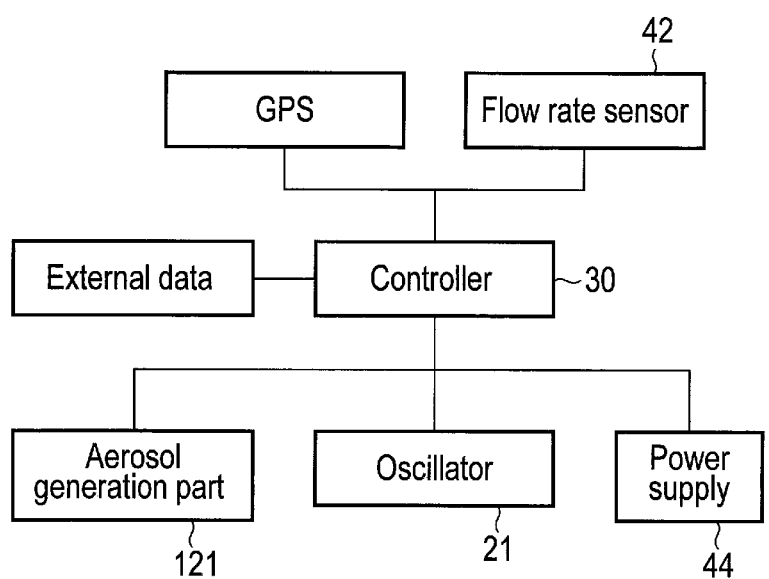
F I G. 9

FLAVOR INHALER

CROSS-REFERENCE TO RELATED APPLICATIONS

This application is a Continuation Application of PCT Application No. PCT/JP2016/072982, filed Aug. 4, 2016, the entire contents of which are incorporated herein by reference.

BACKGROUND OF THE INVENTION

1. Field of the Invention

The present invention relates generally to a flavor inhaler.

2. Description of the Related Art

Various types of flavor inhaler, for example, electronic cigarettes, have been proposed as smoking tools for tasting tobacco-like flavors.

Such electronic cigarettes generate aerosol from flavor generation media containing flavoring substances, and offer experiences similar to smoking tobacco through inhalation of the aerosol.

BRIEF SUMMARY OF THE INVENTION

In recent years, users' tastes of the electronic cigarettes are diversifying, and the users' tastes have not yet been satisfied only by normal smoking experiences.

An object of the present invention is to provide a flavor inhaler which brings about new feelings that are unprecedented.

According to the present invention, a flavor inhaler comprising: a flavor releasing unit comprising at least one holding part for accommodating a flavor component and an aerosol-forming substrate, an aerosol generation part which generates aerosol containing the flavor component from contents of the holding part, and a flavor providing part which is configured to direct the aerosol generated by the aerosol generation part to a user; a speaker unit comprising an oscillator which forms a sound wave, and a speaker interface which transmits the sound wave from the oscillator to a skull of the user; and a controller which controls the flavor releasing unit and the speaker unit so as to coordinate generation of the aerosol and formation of the sound wave is provided.

According to the present invention, a flavor inhaler with which an auditory stimulus by bone conduction and a tactile stimulus by oscillations can be perceived at the same time that aerosol containing a flavor component is inhaled. Accordingly, for example, a flavor inhaler which can satisfy users' tastes more can be provided.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 5 is a block diagram showing an example of a structure of the flavor inhaler according to the embodiment.

FIG. 6 is a flowchart showing an example of basic operation of an example of the flavor inhaler.

FIG. 9 is a block diagram showing an example of a structure of the flavor inhaler according to the third embodiment.

DETAILED DESCRIPTION OF THE INVENTION

Figure 1:
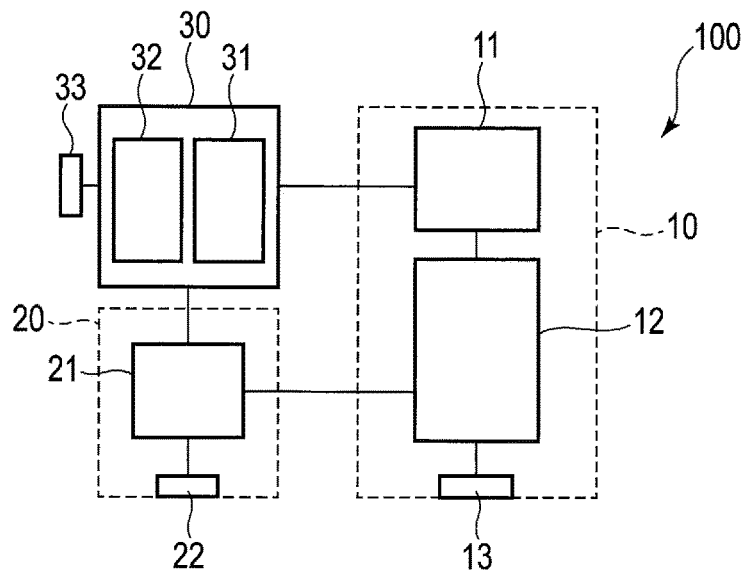
FIG. 1 is a block diagram showing an example of a main structure of a flavor inhaler according to a first embodiment.

Some embodiments will be described hereinafter with reference to the accompanying drawings. The same or similar structures are denoted by the same reference numerals throughout the embodiments, and duplicate explanations are omitted. In addition, each figure is a schematic diagram for promoting understanding of the embodiments, and its shape, dimensions, ratio, etc., are different from those in reality. Further, in the present specification, the terms "upstream" and "downstream" are used as appropriate, with respect to the direction of a flow of aerosol generated when a flavor inhaler is used.

First Embodiment

Figure 2:
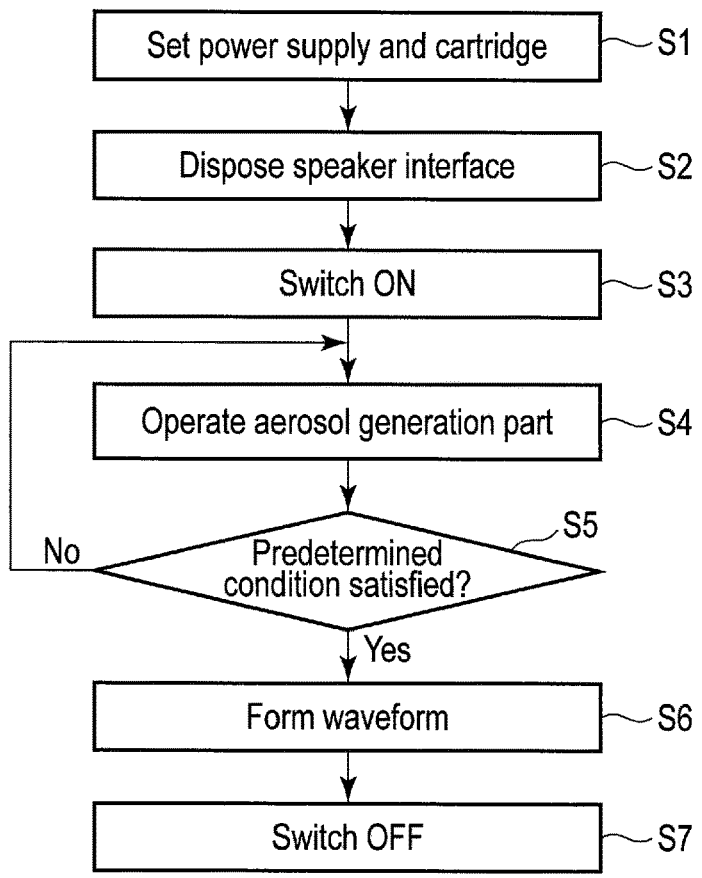
FIG. 2 is a flowchart showing an example of a method of using the flavor inhaler.

A flavor inhaler 100 according to a first embodiment will be described in detail with reference to FIG. 1 and FIG. 2. FIG. 1 is a block diagram showing an example of a main structure of the flavor inhaler according to the first embodiment. FIG. 2 is a flowchart showing an example of a method of using the flavor inhaler.

The flavor inhaler 100 according to the first embodiment comprises, as the main structure, a flavor releasing unit 10 which generates aerosol containing a flavor component, a speaker unit 20 which forms sound waves and which transmits them to a user's skull, and a controller 30 which controls the flavor releasing unit 10 and the speaker unit 20 and which coordinates generation of aerosol and formation of sound waves (FIG. 1).

The flavor releasing unit 10 comprises a holding part 11 for accommodating a flavor component and an aerosol-forming substrate, an aerosol generation part 12 which generates aerosol containing a flavor component from contents of the holding part, and a flavor providing part 13 which directs the generated aerosol to the user. The speaker unit 20 comprises an oscillator 21 which forms sound waves, and a speaker interface 22 which transmits the formed sound waves to the user's skull.

The controller 30, for example, comprises a control part 31 which controls the flavor releasing unit 10 and the speaker unit 20 and a memory 32 which keeps a program for controlling the control part 31, in order that the generation of aerosol and the formation of sound waves coordinate. The control part 31 and the memory 32 are electrically connected to each other. The controller 30, the flavor releasing unit 10, and the speaker unit 20 are electrically connected to each other.

The flavor inhaler 100 can further comprise an electrical interface 33 which is electrically connected to the controller 30. The electrical interface 33 is an interface for communicating with the outside. Via the electrical interface 33, power may be supplied, sound information for forming sound waves may be supplied, and a program for controlling the controller 30 may be supplied. Further, the flavor inhaler 100 can comprise a switch for inputting an operation start signal to the controller 30.

The flavor inhaler 100 can further comprise a power supply (not shown in the figures) for supplying power to the flavor releasing unit 10, the speaker unit 20, and the controller 30. The power supply may be, for example, a battery. For example, if a rechargeable battery is used, charging can be performed via the electrical interface 33.

The use of the flavor inhaler 100 according to the present embodiment can be implemented as follows.

Prior to use, the power supply, for example, a battery, is set in the flavor inhaler 100, and then, a flavor component and an aerosol-forming substrate are accommodated in the holding part 11 (S1). The holding part 11 itself may be a container. In this case, a flavor component and an aerosol-forming substrate can be accommodated in the container. Alternatively, the holding part 11 may be configured to support a container such as a cartridge. In this case, it is only necessary that a cartridge accommodating a flavor component and an aerosol-forming substrate be set in the holding part 11. This process may be carried out by the user or by a person providing the flavor inhaler 100 to the user. For example, the process may be carried out by a supplier before a product is offered to a consumer, or may be carried out by the consumer before it is used.

A wick (not shown in the figures) is provided in the holding part 11, and the wick communicates with the aerosol generation part 12. It is only necessary that the wick be disposed, such that at least a part of the wick contacts the aerosol-forming substrate of the holding part 11. The wick can supply the aerosol-forming substrate which the wick contacts to the aerosol generation part 12 by means of capillarity. A material of the wick may be any material that can cause capillarity. For example, the wick can be a porous body formed of a material such as glass or ceramics, or filaments.

The user disposes the speaker interface 22 in a predetermined region (S2). Next, the user inputs an operation start signal to the controller 30 by turning on an external switch (not shown in the figures) (S3). Alternatively, the flavor inhaler 100 comprises a flow rate sensor (not shown in the figures) in inside, so that when the flow rate sensor senses that the user inhales air from the flavor providing part 13, the flavor inhaler 100 is activated and the operation start signal is input to the controller 30.

The control part 31, which receives the signal, activates the aerosol generation part 12 in accordance with a program stored in the memory 32 (S4). The aerosol generation part 12 can comprise, for example, a heating coil. For example, the heating coil is wound around the wick. The heating coil is connected to the power supply by a wire (not shown in the figures). The aerosol-forming substrate containing the flavor component, which is supplied from the holding part 11 to the aerosol generation part 12 by means of the capillarity of the wick, is heated by the heating coil, and forms aerosol containing a flavor component. The formed aerosol is transmitted to the flavor providing part 13. The flavor providing part 13 is configured to direct the aerosol to the user. For example, the flavor providing part 13 may comprise a mouthpiece, from which the user inhales a flavor component.

Under the control of the control part 31, which obeys a predetermined condition for coordination with control of formation of aerosol (S5), the oscillator 21 forms sound waves (S6). For example, in the step of S5, the control part 31 determines whether or not the predetermined condition is satisfied. If it is determined that the condition is not satisfied, the aerosol generation part 12 is kept operating. If it is determined that the condition is satisfied, the control part 31 transmits a signal to the oscillator 21 and causes oscillator 21 to form sound waves (S6).

The formed sound waves are transmitted to the speaker interface 22. The speaker interface 22 is disposed in advance in a predetermined region that is suitable for transmitting the sound waves to the user's skull. Thus, the user who receives the sound waves from the speaker interface 22 to the skull perceives the sound waves that have reached an auditory organ via bone conduction as a sound signal.

If the predetermined condition is satisfied and the user judges that the switch should be turned off, the user turns off the external switch and stops the operation of the aerosol generation part 12 and the oscillator 21 (S7).

For example, the predetermined condition can be whether or not the aerosol-forming substrate containing the flavor component that should be kept in the holding part 11 is left in the holding part 11. For example, in this case, the flavor inhaler 100 can further comprise a sensor which detects the remaining amount of contents kept in the holding part 11. For example, if the aerosol-forming substrate is a conductive substance, a current is constantly applied thereto, and the remaining amount can be detected by a sensor which detects that the current is shut off, for example, an electrode. The flavor inhaler 100 comprising such a sensor also can be provided as one embodiment. Furthermore, in this case, the flavor inhaler 100 can comprise, for example, a remaining-amount detection circuit which is electrically connected to the control part 31.

By virtue of the above-described structure, the user can perceive an auditory stimulus by bone conduction and a tactile stimulus by oscillations at the same time that the user inhales aerosol containing a flavor component. The user's taste is thereby more satisfied.

Second Embodiment

Figure 3:
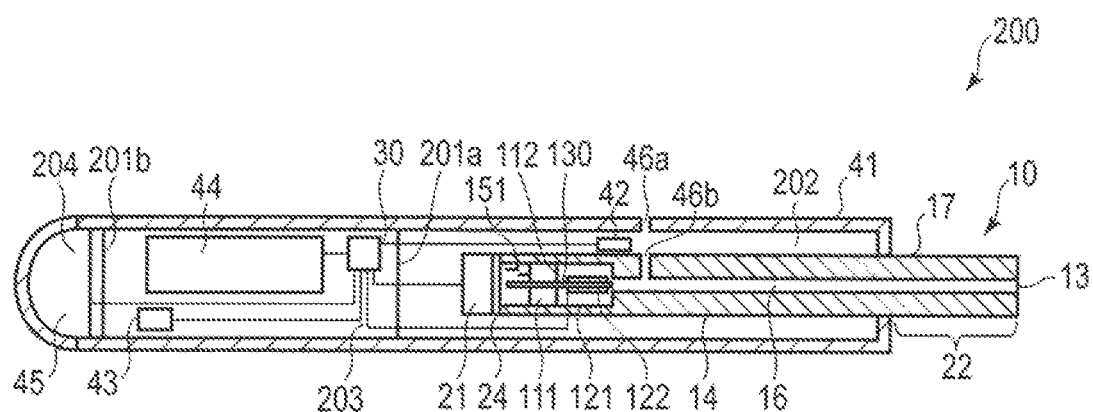
FIG. 3 is a schematic cross-sectional view showing a main structure of a flavor inhaler according to a second embodiment.
Figure 4:
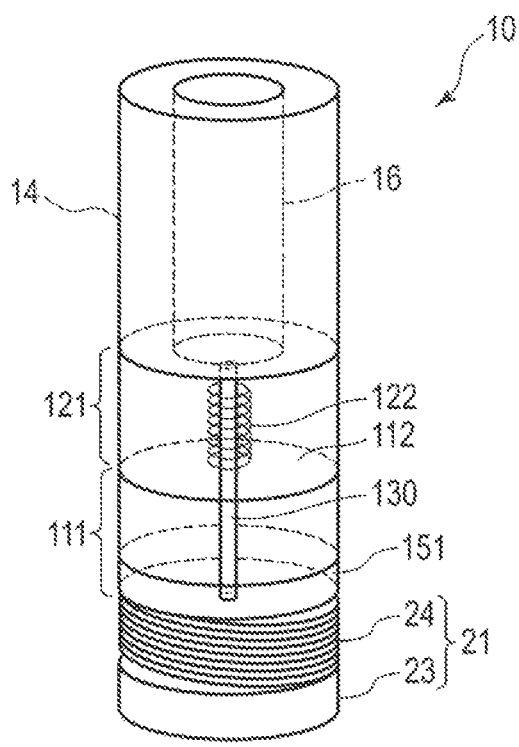
FIG. 4 is an enlarged schematic view showing examples of an oscillator, a holding part, and an aerosol generation part.

FIG. 3 is a schematic cross-sectional view of a flavor inhaler 200 according to a second embodiment, and shows an example of a so-called cigarette type flavor inhaler having a cylindrical shape. FIG. 4 is an enlarged perspective view showing the structure of a holding part 111, an aerosol generation part 121, and an oscillator 21 of the flavor inhaler 200.

The flavor inhaler 200 according to the second embodiment is an example of the cigarette type flavor inhaler further comprising a conduit 14, a housing 41, a flow rate sensor 42, an acceleration sensor 43, a power supply 44, and a light emitting part 45, in addition to the structural elements of the flavor inhaler 100 according to the above-described first embodiment.

The housing 41 of the flavor inhaler 200 is a slender hollow housing, one end of which is rounded and closed. The other end thereof is partly opened, and a mouthpiece part 17 projects from this opening. The tip portion of the mouthpiece part 17 is a mouthpiece as a flavor providing part 13. This structure as a whole forms a cigarette type (cylindrical) outer shape. This can be a so-called electronic cigarette.

The housing 41 can be formed of, for example, resin, metal, ceramics, or wood.

The inside of the housing 41 is divided by two partitions 201a and 201b into three chambers, that is, a first chamber 202, a second chamber 203, and a third chamber 204.

The flavor releasing unit 10 may have the form of a removable cartridge. The form of a cartridge enables the flavor releasing unit 10 to be replaced by a new flavor releasing unit, when an aerosol-forming substrate 151 and/or a flavor component is used up. The holding part 111 is disposed inside an end portion on the upstream side of the flavor releasing unit 10. The aerosol-forming substrate 151 containing a flavor component is accommodated in the holding part 111. In the present embodiment, an example of container holding the aerosol-forming substrate 151, which is a liquid, is shown as the holding part 111.

As the aerosol-forming substrate 151 and the flavor component, substances extracted from various natural products and/or their constituents can be selected depending on the intended use. As the flavor component, for example, menthol, caffeine, a precursor of glycoside, etc., which generates a flavor by thermal decomposition, or a tobacco component such as a tobacco extract component or a tobacco smoke condensate component can be used. As the aerosol-forming substrate 151, polyol such as glycerin or propylene glycol, lower alcohol, saccharide, or a mixture thereof can be used. Also, cotton, etc., may be impregnated with the aerosol-forming substrate 151, and accommodated in the holding part 111.

The holding part 111 and the aerosol generation part 121 are divided by a partition 112. A wick 130 is disposed to penetrate a central portion of the partition 112 and to communicate with the holding part 111 and the aerosol generation part 121. It is only necessary that at least a part of the upstream side of the wick 130 be in contact with the aerosol-forming substrate 151 in the holding part 111. In the examples shown in FIG. 3 and FIG. 4, the upstream side of the wick 130 is impregnated with the aerosol-forming substrate 151. The aerosol-forming substrate 151, which is in contact with the wick 130, soaks into the wick 130 and is supplied from the holding part 111 to the aerosol generation part 121 by means of capillarity. The downstream end portion of the wick 130 extends to the aerosol generation part 121 in the vicinity of a flow channel 16. A material of the wick 130 may be any material that can cause capillarity. The wick 30 can be composed of, for example, a porous body formed of a material such as glass or ceramics, or a number of filaments. In the present embodiment, an example of the wick 130, which extends straight from the downstream side to the upstream side, has been described. However, the shape of the wick 130 may be changed as appropriate depending on the mode of use of the flavor inhaler 200.

The aerosol generation part 121 is disposed further downstream than the holding part 111. The aerosol generation part 121 comprises a heating element 122 as a heating material. The heating element 122 may be made of, for example, a Nichrome wire. In the example shown in FIG. 4, the heating element 122 is disposed at the downstream side of the wick 130, and has a spiral form along its outer periphery. Further, in this example, the heating element 122 is not in contact with the wick 130.

Any well-known mechanism may be used as the aerosol generation part 121 itself, as along as it is an aerosol generation mechanism which generates aerosol containing a flavor component from the aerosol-forming substrate 151 held in the holding part 111. That is, an example of use of the aerosol generation part 121, which comprises the heating element 122, has been herein described. However, the aerosol generation part 121 is not limited to such an aerosol generating mechanism in which a heating member such as the heating element 122 is used. The aerosol generation part 121 may be, for example, an oscillating member which generates aerosol by oscillating the aerosol-forming substrate 151.

The conduit 14 is disposed at the downstream end of the aerosol generation part 121. The conduit 14 is a hollow tube, and comprises the flow channel 16 inside thereof. The aerosol generation part 121 disperses aerosol containing a flavor component into gas inside the flow channel 16 by heating, with the heating element 122, the aerosol-forming substrate 151 containing the flavor component, which is supplied from the holding part 111 to the aerosol generation part 121 by means of the capillarity of the wick 130. Aerosol generated by the aerosol generation part 121 passes through the flow channel 16 and is transmitted to the mouthpiece part 17. A user can inhale aerosol from the mouthpiece part 17.

The oscillator 21 is disposed on the outside of the bottom portion of the flavor releasing unit 10 so as to be in contact with the outer bottom portion of the holding part 111.

The oscillator 21 comprises a voice coil 24 and a magnet 23. The oscillator 21 can produce oscillations by operating the voice coil 24 with a magnet field formed by the magnet 23.

The magnet 23 itself may be any well-known magnet, and can be adjusted as appropriate so as to transmit magnetic force to the magnetic field efficiently. The magnet 23 can be formed of, for example, a metallic material such as iron. In addition, the magnet 23 can be, for example, a cylindrically molded permanent magnet.

As described above, the oscillator 21 is disposed to be in contact with the holding part 111. Thus, when the oscillator 21 oscillates, its oscillations reach the aerosol-forming substrate 151 accommodated in the holding part 111. The aerosol-forming substrate 151 thereby can be agitated. Such agitation can prevent a solute included in the aerosol-forming substrate 151 from precipitating. At the same time, the oscillations of the aerosol-forming substrate 151 facilitate the movement of the aerosol-forming substrate 151 to the aerosol generation part 121. Aerosol thereby can be formed efficiently. To achieve such an advantage, it is only necessary that at least a part of the oscillator 21 be in contact with the holding part 111 directly or indirectly so that oscillations produced by the oscillator 21 propagate to the holding part 111.

The conduit 14 transmits sound waves formed by the oscillator 21 to the mouthpiece part 17. The mouthpiece part 17 functions as a speaker interface 22 which transmits sound waves to the user's skull via the user's teeth. When the user holds the mouthpiece part 17 in the mouth, and the mouthpiece part 17 and the user's teeth are in contact with each other, oscillations from the oscillator 21 are transmitted to the user's teeth via the conduit 14 (that is, the speaker interface 22) as sound waves. The oscillations transmitted to the teeth pass through the skull, and oscillate auditory ossicles of ears. The user thereby hears the oscillations as sound.

A first intake port 46a leading to the outside is formed in a wall surface in an area corresponding to the first chamber 202 of the flavor inhaler 200. The first intake port 46a penetrates a wall surface of the housing 41, and can take air into the housing 41 or release air from the housing 41 to the outside. In addition, a second intake port 46b is also provided in a wall surface of the conduit 14. Furthermore, the second intake port 46b is disposed on a wall surface of the conduit 14. The second intake port 46b is provided in a portion corresponding to the area of the holding part 111 of the conduit 14. When the user inhales air from the mouthpiece 13, outside air passes through the first intake port 46a, and is supplied to the inside of the housing 41. Air supplied to the inside of the housing 41 passes through the second intake port 46b, and is supplied to the inside of the flow channel 16. This air is mixed with aerosol from the holding part 111, and released from the mouthpiece 13 to the user. A filter may be provided to cover the second intake port 46b from the inside or the outside of the conduit 14. The second intake port 46b enables the user to inhale aerosol, and is not essential. Its opening portion can be changed as desired.

The flow rate sensor 42, which is configured to detect a change in airflow in the housing 41 caused by the user's use of the flavor inhaler 200, is disposed in the housing 41 in the vicinity of the first intake port 46a. The flow rate sensor 42 detects the user's puff by detecting the magnitude of airflow and/or the direction of airflow. The "puff" herein means the user's act of generating airflow, which includes inhaling from the flavor inhaler 200 and blowing into the flavor inhaler 200. The flow rate sensor 42 can be, for example, a pressure sensor. The pressure sensor can detect a decline in the pressure in the flavor inhaler 200 caused by the user's inhalation or a rise in the pressure in the flavor inhaler 200 caused by the user's blow. The flow rate sensor 42 is electrically connected to a controller 30. A signal detected by the flow rate sensor 42 can be transmitted to the controller 30 via a puff detection circuit (not shown in the figures).

In the second chamber 203, the controller 30, the acceleration sensor 43, and the power supply 44 are disposed. The partition 201a exists between the second chamber 203 and the inside of the above-described first chamber 202. Thus, a member which is susceptible to water or for which a clean environment is suitable, such as the controller 30 or the power supply 44, can be maintained more properly.

As the acceleration sensor 43 itself, any well-known acceleration sensor can be used. The acceleration sensor 43 can detect oscillations and an inclination of the flavor inhaler 200. The acceleration sensor 43 is electrically connected to the controller 30. A signal detected by the acceleration sensor 43 can be transmitted to the controller 30 via an inclination detection circuit (not shown in the figures).

The controller 30 can determine whether or not a signal detected by the flow rate sensor 42 and/or the acceleration sensor 43 satisfies a predetermined condition, and control the flavor releasing unit 10 and/or a speaker unit or cooperation between the flavor releasing unit 10 and the speaker unit, based on the determination. The predetermined condition may be, for example, a predetermined threshold value. In this case, information obtained by a sensor and the threshold value are compared, so that a result of the comparison can be reflected in a control process. Correspondence between each condition and process can be stored in the memory as a table in association with each other in advance.

The light emitting part 45 is disposed in the third chamber 204. The light emitting part 45 comprises, for example, an LED or a fluorescent lamp. The light emitting part 45 is electrically connected to the controller 30. The light emitting part 45 can be configured to emit light, when the controller 30 determines that the predetermined condition is satisfied, via a light emitting circuit (not shown in the figures).

The power supply 44 supplies power to each member of the flavor inhaler 200, for example, the heating element 122, the oscillator 21, the flow rate sensor 42, the light emitting part 45, and the controller 30. The supply of power to each member can be controlled by the controller 30.

The flavor inhaler 200 can comprise a geographic position information device, which is not shown in the figures, in the housing 41. The geographic position information device acquires current geographic position information of the user and the flavor inhaler 200. As the geographic position information device itself, any well-known device, for example a GPS, can be used.

The controller 30 and each structural member included in the flavor inhaler 200 are electrically connected to each other (FIG. 5). The controller 30 can, for example, receive signals from the geographic position information device, the acceleration sensor 43, and the flow rate sensor 42, and use these signals as a basis for determination to make a selection or determination in a series of processes. The operation of the aerosol generation part 121, the oscillator 21, and the light emitting part 45 can be controlled in accordance with information based on these signals by the controller 30 and corresponding control circuits.

The structure of the controller 30 can be the same as in the above-described first embodiment. For example, the memory can temporarily, continuously, or perpetually store or record a signal from each member of the flavor inhaler 200, information received from the outside of the flavor inhaler 200, a program showing a flow of a predetermined process, and a condition as a basis for determination included in the process, for example, information such as a threshold value or a table in which the condition and the process are associated. The memory can, for example, keep sound-wave information, for example, a wavelength, a frequency, the number of times sound waves occur, a timing of formation of sound waves, a condition of occurrence, and a time of formation of sound waves; sound information, for example, music information, voice information, sound-effects information, and sound waves; the number of times the user inhales, the frequency of inhalation, the amount of inhalation, and the strength of inhalation, in relation to the flow rate sensor; and process information of each member that should be controlled by the controller 30 in relation to these, for example, a timing of operation start, an operation time, a stop timing, a stop time, and information on adjustment between a plurality of members. However, what can be kept in the memory is not limited to these. The above information may have any form, such as a table or a list.

For example, a signal detected by the acceleration sensor 43 is transmitted to the controller 30 with information on an inclination or oscillations of the flavor inhaler 200 as a detection signal. The controller 30 can control the operation of the aerosol generation part 121, the oscillator 21, and the light emitting part 45 in accordance with the detection signal from the acceleration sensor 43. For example, the controller 30 can adjust sound waves from the oscillator 21, aerosol from the aerosol generation part 121, formation of light of the light emitting part 45, a duration of formation, a formation stop timing, etc. For example, the controller 30 can stop the operation of the aerosol generation part 121 and inform the user of an abnormality by emitting a sound from the oscillator 21 and turning on or blinking the light emitting part 45, if the acceleration sensor 43 detects an abnormal inclination of the flavor inhaler 200.

A detection signal from the flow rate sensor 42 is transmitted to the controller 30 with information on the user's puff motion as an output signal. The controller 30 can control the operation of the aerosol generation part 121, the oscillator 21, the light emitting part 45, etc., in accordance with the output signal from the flow rate sensor 42. The controller 30 can adjust sound waves from the oscillator 21, aerosol from the aerosol generation part 121, and formation of light of the light emitting part 45, a duration of formation, a formation stop, etc., based on the signal from the flow rate sensor 42.

The GPS device detects geographic position information of the flavor inhaler 200, and transmits the geographic position information to the controller as an output signal. The controller 30 can control the operation of the aerosol generation part 121, the oscillator 21, the light emitting part 45, etc., in accordance with the output signal.

A communication interface (not shown in the figures) can be connected to an external network, for example, Bluetooth, infrared communication, or a local area network (LAN). The flavor inhaler 200 thereby can transmit and receive data to and from the outside. The communication interface may be a wire or a wireless. As shown in FIG. 5, the controller 30 can control each member of the flavor inhaler 200, based on information received from the outside (external data). In addition, the controller 30 may be configured to be controlled from the outside via the communication interface 33. Information received via the communication interface 33 can be kept in the memory. For example, the flavor inhaler 200 can connect to another communication device such as a smartphone via the communication interface, control each member of the flavor inhaler 200 by the other communication device, and change sound-wave information, the amount of generated aerosol, etc.

The flavor inhaler 200 can, for example, operate in accordance with a flowchart shown in FIG. 6.

The user turns on in advance a main switch of the flavor inhaler 200. Accordingly, standby power from the power supply 44 is supplied to the controller 30, and the flavor inhaler 200 is kept in a standby state (S11). The user holds the mouthpiece part 17 in the mouth, and inhales air from the mouthpiece 13. The flow rate sensor 42 detects airflow from the first intake port 46*a* to the inside of the housing 41 (S12). The flow rate sensor 42 transmits a detected signal to the controller 30. The controller 30 cancels the standby state (S13), increases the amount of power supplied from the power supply 44, and supplies power to the aerosol generation part 121, the oscillator 21, the flow rate sensor 42, and the acceleration sensor 43 to cause them to operate (S14). Generated aerosol containing a flavor component and sound waves are provided to the user from the mouthpiece 13 and the speaker interface 22, respectively (S14). The flow rate sensor 42 and the acceleration sensor 43 each monitor the state of the flavor inhaler 200, and transmit an obtained result to the controller 30. The controller 30 determines whether or not an obtained signal satisfies a predetermined condition.

Alternatively, the flow rate sensor 42 and the acceleration sensor 43 each monitor the state of the flavor inhaler 200, and transmit an obtained result to each analytic circuit (not shown in the figures). The analytic circuits determine whether or not an obtained signal satisfies a predetermined condition, and transmit a signal to the controller 30 if it is determined that the predetermined condition is satisfied (not shown in the figures). For example, the flow rate sensor 42 monitors airflow from the first intake port 46*a* to the inside of the housing 41, and transmits a result of the monitoring to the controller 30 periodically. The controller 30, for example, calculates a first inhalation frequency of the user in accordance with a predetermined calculation formula. The acceleration sensor 43 monitors an inclination of the flavor inhaler 200, and transmits a result of the monitoring to the controller periodically. The controller 30, for example, calculates a second inhalation frequency of the user in accordance with a predetermined calculation formula. The controller 30 determines the degree to which the user intends to continue inhaling, based on the first and second frequencies, a table kept in advance in the memory, etc. The controller 30 compares the obtained degree and a predetermined threshold value (S15). As a result of the comparison, if the degree is less than the threshold value, that is, when the end of the inhalation is determined to be close, the controller 30 reduces the amount of formed sound waves from the oscillator 21 (S16). The controller 30 executes control so that the aerosol generation part 121 forms a predetermined amount of aerosol just after the detection of airflow by the flow rate sensor 42. If there is not the detection of airflow by the flow rate sensor 42 for a predetermined time and the controller 30 determines that the end of the inhaling (S17), the amount of power supplied from the power supply 44 is reduced, and the flavor inhaler 200 returns to the standby state (S11).

According to the above-described present embodiment, the transmission of sound information by bone conduction and the inhalation of aerosol containing a flavor coordinate with each other and are provided to the user. This enables the user to have an unprecedented smoking experience.

The above-described example is an example in which the controller 30 controls the aerosol generation part 121 and the oscillator 21 to cause them to cooperate with each other, based on monitoring signals from the two sensors of the flow rate sensor 42 and the acceleration sensor 43, thereby controlling the flavor releasing unit 10 and the speaker unit. However, the present embodiment is not limited to this. The flavor inhaler 200 may comprise one of the flow rate sensor 42 and the acceleration sensor 43, so that the controller 30 controls the aerosol generation part 121 and the oscillator 21 to cause them to cooperate with each other based on a signal from the one of the flow rate sensor 42 and the acceleration sensor 43. Moreover, the flavor inhaler 200 may comprise the flow rate sensor 42 and/or the acceleration sensor 43 and another sensor in combination.

Further, in the above description, an example of the flavor inhaler 200, which has the form of a cigarette (cylindrical shape), has been shown. However, the outer shape of the housing is not limited to this. The housing may have the form of a cigar, a prism, a pyramid, a cone, or a body of revolution thereof, which has an outside diameter at least partly greater than the form of a cigarette (cylindrical shape). In addition, providing that the flavor releasing unit 10 and the speaker unit 20 are controlled, such that the aerosol generation part 121 and the oscillator 21 are controlled to cooperate with each other, the plurality of members constituting the flavor inhaler 200 may be independently accommodated in a plurality of independent housings.

Moreover, the flavor inhaler 200 can use the flow rate sensor 42, the acceleration sensor 43, and the GPS, in order to control generation of aerosol and/or oscillations of the oscillator 21 while it is used. For example, if the acceleration sensor 43 detects a change in the inclination of the flavor inhaler 200, a signal is output from the acceleration sensor 43 to the controller 30, and the controller 30 controls the aerosol generation part 121 and/or the oscillator 21 based on the output signal. For example, in accordance with the inclination of the flavor inhaler 200, the output of the aerosol generation part 121 can be adjusted to control the amount of generated aerosol. If the inclination of the flavor inhaler 200 is large, the amount of generated aerosol can be made larger, and if the inclination of the flavor inhaler is small, the amount of generated aerosol can be made smaller. Furthermore, the output of the oscillator 21 can be adjusted and controlled to generate bone conduction sound varying according to the inclination of the flavor inhaler 200. Moreover, if the acceleration sensor 43 detects an abnormal inclination of the flavor inhaler 200, the controller 30 can cause the aerosol generation part 121 to stop operating, and notify the user of an abnormality with oscillations of the oscillator 21.

With the flavor inhaler 200 according to the present embodiment, the user can hear bone conduction sound, for example, by bringing the mouthpiece part 17 into contact with the user's head or jaw, even without bringing the mouthpiece part 17 into contact with the user's teeth.

In addition, the flavor inhaler 200 is oscillated by the oscillator 21. The user can perceive oscillations with fingers or lips when holding the flavor inhaler 200 between the fingers or lips. Thus, with the flavor inhaler 200 according to the present embodiment, not only auditory pleasure by bone conduction but also tactile pleasure by oscillations can be perceived. The user's taste can be more satisfied.

In addition, since bone conduction sound is used as sound waves in the flavor inhaler 200 according to the present embodiment, bone conduction sound from the speaker unit 20 can be heard without being interfered with by, for example, ambient noise.

Third Embodiment

Figure 7:
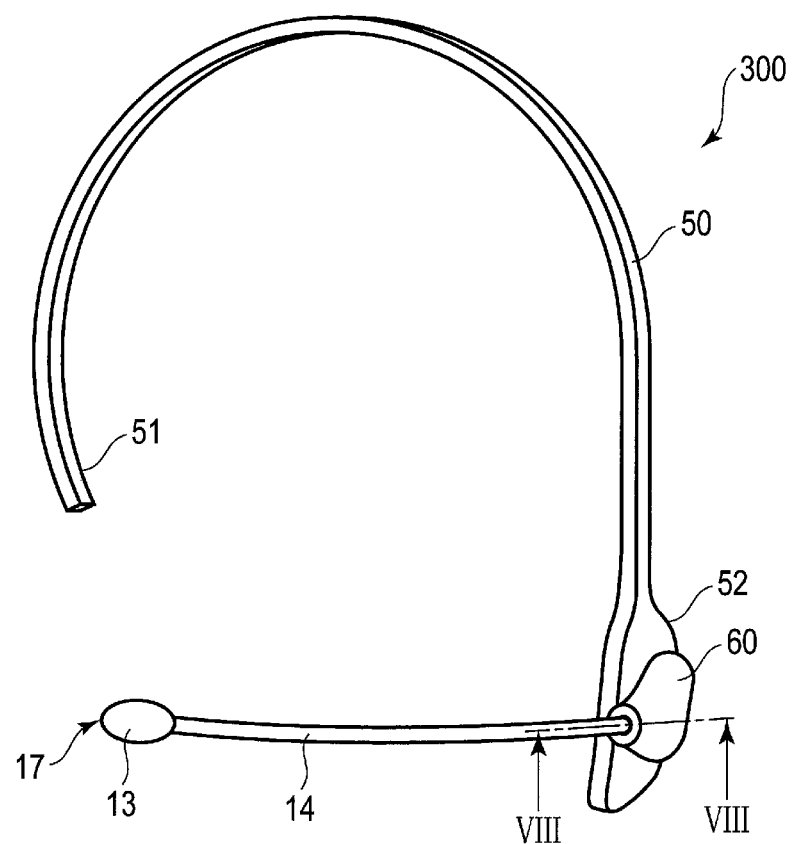
FIG. 7 is a schematic perspective view showing an example of a flavor inhaler according to a third embodiment.
Figure 8:
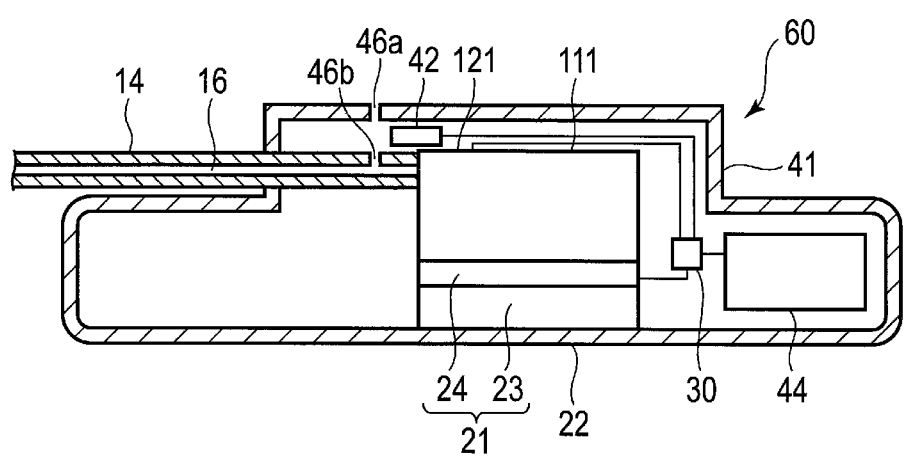
FIG. 8 is a schematic cross-sectional view along line VIII-VIII of FIG. 7.

A flavor inhaler according to a third embodiment will be described next with reference to FIG. 7, FIG. 8, and FIG. 9. FIG. 7 is a schematic perspective view showing an example of the flavor inhaler according to the third embodiment. FIG. 8 is a schematic cross-sectional view along line VIII-VIII of FIG. 7. FIG. 9 is a block diagram showing an example of the structure of the flavor inhaler according to the third embodiment.

The flavor inhaler 300 according to the third embodiment is a headphone type flavor inhaler 300. The flavor inhaler 300 according to the third embodiment is different in the entire shape from the flavor inhaler 200 according to the second embodiment. However, the basic structure of the flavor inhaler 300 can be shown in FIG. 1 as in the case of the first embodiment. The flavor inhaler 300 comprises a U-shaped headband part 50 and a flavor inhaler main body 60.

The headband part 50 has a semicircular arc shape, and can be formed of, for example, elastic plastic or metal. The headband part 50 comprises a first end portion 51 and a second end portion 52, and can be fixed to a user's head by holding the user's head between these two end portions 51 and 52. Thus, the flavor inhaler main body 60 is fixed to the user's head. The flavor inhaler main body 60 is disposed at the end portion 52 of the two end portions 51 and 52. The flavor inhaler 300 is preferably designed so as to bring the flavor inhaler main body 60 into contact with the skin in the vicinity of a bone (mastoid) behind the user's ear.

As shown in FIG. 8, the flavor inhaler main body 60 comprises a housing 41, a holding part 111, an oscillator 21, a conduit 14, a flow channel 16, a controller 30, and a power supply 44. The housing 41 is provided with an intake port 46a, from which air can be taken into the housing 41.

The oscillator 21 is disposed on the inside of a surface contacting the user's head (speaker interface 22) of the housing 41. The structure of the oscillator 21 may be the same as in the first embodiment. When the oscillator 21 oscillates, oscillations of the oscillator 21 are transmitted to the user via the speaker interface 22, and the user can hear the oscillations as bone conduction sound.

The holding part 111 is provided on an upper surface of the oscillator 21. An aerosol-forming substrate (not shown in the figures) containing a flavor component is held in the inside of the holding part 111. Further, an aerosol generation part 121 is provided on the downstream side of the holding part 111.

As shown in FIG. 9, the controller 30 is electrically connected to each structural member. For example, the controller 30 is electrically connected to a geographic position information device (GPS), an acceleration sensor 43, a flow rate sensor 42, etc., and can receive signals from these members. In addition, for example, the controller 30 can control the operation of the aerosol generation part 121, the oscillator 21, the power supply 44, etc., based on signals from the geographic position information device (GPS), the acceleration sensor 43, the flow rate sensor 42, etc. The functions, etc., of each structural member are the same as those described with respect to the first embodiment. Thus, an explanation thereof is omitted.

As shown in FIG. 7, the conduit 14 extends from a side surface of the housing 41, for example, to the vicinity of the user's nose or mouth. A flavor providing part 13 is provided at a tip of the conduit 14. Aerosol generated by the aerosol generation part 121 in the holding part 11 passes through the flow channel 16 in the conduit 14, and is released to the user from the flavor providing part 13. The user can inhale aerosol containing a flavor by holding the end portion of the conduit 14 in the mouth, and inhaling air.

The flavor inhaler 300 according to the third embodiment allows the user to inhale aerosol without holding the flavor inhaler in the hand, as well as having the advantages described with respect to the first embodiment. Thus, the flavor inhaler can be used without stopping other works.

Further, in the description of the flavor inhaler 300 according to the third embodiment, an example in which the user can inhale aerosol containing a flavor by holding a mouthpiece part 17 at the tip portion of the conduit 14 and inhaling air has been given. However, the flavor inhaler 300 may be a form in which aerosol containing a flavor to jet from the flavor providing part 13 to a space in the vicinity of the user's mouth and/or nose, thereby allowing the user to inhale aerosol containing a flavor component.

Also, in the first to third embodiments, a form in which the flavor releasing unit and the speaker unit are accommodated in the housing 41 is shown. However, the flavor releasing unit and the speaker unit may be accommodated in separate housings, respectively. For example, it is possible that the flavor releasing unit is accommodated in a cigarette type first housing and the speaker unit is accommodated in a headphone type second housing.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A flavor inhaler comprising:
a housing;
a flavor releasing unit comprising:
at least one holding part for accommodating a flavor component and an aerosol-forming substrate;
an aerosol generation part which generates aerosol containing the flavor component from contents of the holding part; and
a flavor providing part configured to direct the aerosol generated by the aerosol generation part to a user;
a speaker unit which oscillates a skull of the user, comprising:
an oscillator which forms a sound wave; and
a speaker interface which transmits the sound wave from the oscillator to the skull of the user via bone conduction, wherein a first end portion of the speaker interface contacts the oscillator, and a second end portion of the speaker interface is directed outward from the housing and contacts teeth, a head or a jaw of the user; and
a controller which controls the flavor releasing unit and the speaker unit so as to coordinate generation of the aerosol and formation of the sound wave,
wherein the housing accommodates the oscillator, the speaker unit, and the controller.

2. The flavor inhaler of claim 1, wherein the speaker interface comprises a conduit which has one end connected with the aerosol generation part and another end extending outward from inside the housing,
wherein the flavor providing part is provided at the another end of the conduit,
wherein the oscillator is disposed to be at least partly in contact with the at least one holding part, and
wherein an oscillation from the oscillator is imparted to a substance held in the holding part.

3. The flavor inhaler of claim 1, wherein the housing has a cylindrical shape.

4. The flavor inhaler of claim 1, wherein the flavor providing part comprises a mouthpiece, and
wherein the speaker interface exists on an outer surface of the mouthpiece.

5. The flavor inhaler of claim 1, further comprising a flow rate sensor which detects a change in airflow existing or generated inside the flavor inhaler as a first signal, and which outputs the first signal to the controller,
wherein the controller controls the speaker unit and the flavor releasing unit so as to coordinate generation of the sound wave and the aerosol, based on the detected first signal.

6. The flavor inhaler of claim 1, further comprising an acceleration sensor which detects a change in inclination of the flavor inhaler as a second signal, and which outputs the second signal to the controller,
wherein the controller controls the speaker unit and the flavor releasing unit so as to coordinate generation of the sound wave and the aerosol, based on the second signal.

7. The flavor inhaler of claim 1, further comprising a U-shaped headband comprising the housing fixed to one end side,
wherein the headband is configured to impel a first end portion and a second end portion of the headband in a direction in which the first end portion and the second end portion of the headband become closer to each other, and to hold a head of the user, and
wherein the speaker interface exists on the user side at the first end portion of the headband, and extends to be in front of a lower part of a face of the user when the headband is worn on the head of the user.

* * * * *